United States Patent [19]

Stone et al.

[11] Patent Number: 5,461,052
[45] Date of Patent: Oct. 24, 1995

[54] PREVENTION OF MYOPIA BY TRICYCLIC COMPOUNDS

[75] Inventors: Richard A. Stone, Havertown; Alan M. Laties, Philadelphia, both of Pa.

[73] Assignee: The Trustees of the University of Pennsylvania, Philadelphia, Pa.

[21] Appl. No.: 55,202

[22] Filed: Apr. 30, 1993

[51] Int. Cl.⁶ ..................................................... A61K 31/55
[52] U.S. Cl. .......................................... 514/217; 514/912
[58] Field of Search ..................................... 514/217, 912

[56] References Cited

U.S. PATENT DOCUMENTS

| 4,865,599 | 9/1989 | Chiou | 424/427 |
| 5,055,302 | 10/1991 | Laties et al. | 424/427 |
| 5,122,522 | 6/1992 | Laties et al. | 514/220 |
| 5,284,843 | 2/1994 | Stone et al. | 514/213 |

OTHER PUBLICATIONS

The Merck Index Eleventh Edition 1989, pp. 80 and 780.
European Journal of Pharmacology, 190 (1990) 1–9. Ikeda et al.
Hoffmeister, F. and Stille, G. *Psychotropic Agents, Part 1: Antipsychotics and Antidepressants*, Zeelen, F. J., Chapter 16, "Chemistry Structure and Activity", (1980). Springer–Verlag, New York, 1980.

*Primary Examiner*—Zohreh Fay
*Attorney, Agent, or Firm*—Woodcock Washburn Kurtz Mackiewicz & Norris

[57] ABSTRACT

A composition for the inhibition of the abnormal postnatal axial growth of the eye of a maturing animal which comprises a pharmaceutically effective amount of a tricyclic compound, said tricyclic compound present in a carrier or diluent suitable for ocular administration. Suitable tricyclics are tertiary amines, secondary amines, and other active metabolites of tricyclic compounds.

7 Claims, 1 Drawing Sheet

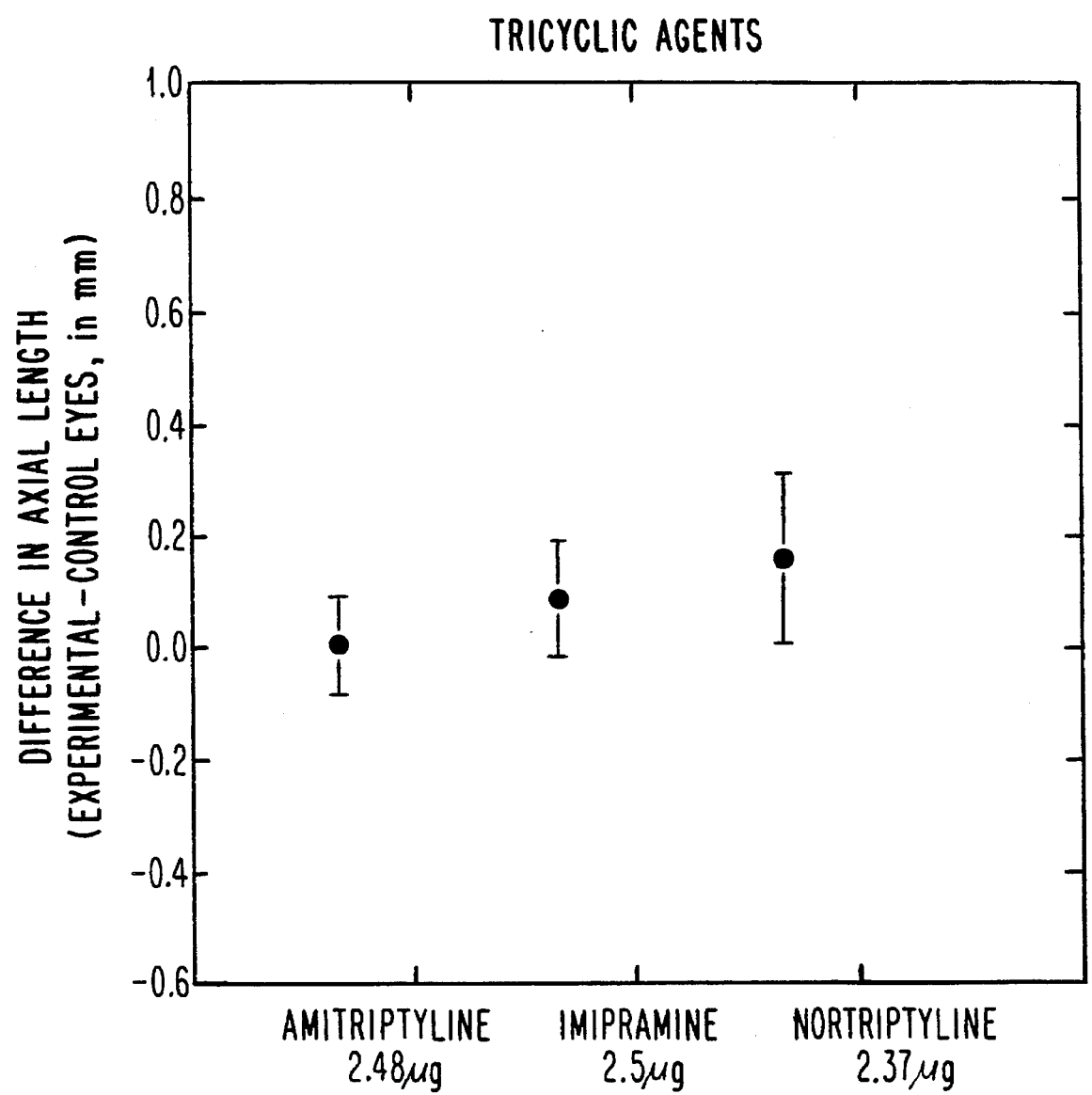

PREVENTION OF MYOPIA BY TRICYCLIC COMPOUNDS

GOVERNMENT SUPPORT

This work was supported in part by research grants from the National Institutes of Health-National Eye Institute, grant numbers EY05454 and EY07354. The United States Government may have certain rights in this invention.

BACKGROUND OF THE INVENTION

This invention relates to control of ocular development and, more particularly, to the treatment of the eye to control the development of myopia (commonly known as nearsightedness).

It has been estimated that about one of every four persons on earth suffers from myopia. About one-half or more of these cases are axial myopia, i.e., an elongation of the eye along the visual axis.

At birth, the human eye is about two-thirds adult size. During the first years of life the eye is relatively short in the axial direction. As a consequence, young children tend to be farsighted. During childhood, as the eye grows, there is a compensatory fine tuning of the optical properties of the cornea and lens to the increasing ocular length. Often the entire process is virtually perfect and no correction is needed for sharp vision at distance; the eye is emmetropic. When regulatory failure in this finely tuned process occurs, it usually goes toward a lengthened eye. As a result, distant images focus in front of the plane of the retina and axial myopia results. If, on the other hand, the regulatory failure leads to an eye whose ocular length is too short, near images focus behind the plane of the retina and the result is hyperopia (commonly known as farsightedness).

Over the years, many theories have been put forth to explain the development of myopia, e.g., inheritance, excessive near work, and environmental influences such as hours of sunshine, diet, etc. From these theories many preventative measures have been proposed including spectacles, eye exercise, eye rest, cycloplegia, and other drug therapies. The clinical literature on the subject is massive.

Based on a theory that substantial use of the eye by children for reading leads to the development of permanent nearsightedness or myopia, many remedies directed at the focussing mechanism at the front of the eye have been proposed. Largely these have been attempts either to block near focus through topical application of drugs or to remove any need for near focus through use of plus lenses that in effect perform the near focus task. Topical drugs that relax the focussing muscle of the eye, the ciliary muscle, are called cycloplegics and have been available for a century.

Some clinical studies have suggested that atropine, a long-acting cycloplegic, applied topically to the eye may retard development of myopia. Atropine treatment, however, is not practical: it causes profound dilation of the pupil, which results in light sensitivity, and its action to inhibit ocular focussing impairs near visual work like reading. In addition, a dilated pupil causes discomfort to the patient.

There is now substantial evidence to validate the worth of an experimental model of myopia and through its use to link the posterior part of the eye, specifically image quality at the retina and hence an extension of the nervous system, to the postnatal regulation of ocular growth. There is significant evidence of myopia resulting in an eye that is subjected to retinal image degradation. It has been shown that axial myopia can be experimentally induced, in either birds or primates, in an eye in which the retina is deprived of formed images, e.g., by suturing the eyelids or wearing an image-diffusing goggle. The experimental myopia induced in primates such as monkeys mimics the common axial myopia of humans.

Thus, the phenomenon of an animal's vision process apparently contributes to the feedback mechanism by which postnatal ocular growth is normally regulated and refractive error is determined. This indicates that this mechanism is neural and likely originates in the retina. Further, there is good evidence that the phenomena lends itself to an assay for potential therapeutic agents.

U.S. Pat. No. 5,055,302, to Laties and Stone, discloses a method of controlling the abnormal postnatal growth of the eye of a maturing animal using vasoactive intestinal peptide (VIP), PH1 or analogues of these peptides. These peptides were found to inhibit axial elongation of a myopic eye.

U.S. Pat. No. 5,122,522, to Laties and Stone, discloses a method of controlling the abnormal postnatal growth of the eye of a maturing animal using pirenzepine. Axial elongation of a myopic eye was inhibited upon application of pirenzepine.

SUMMARY OF THE INVENTION

The present invention provides methods for regulating the growth of an animal's eye. The methods of the invention comprise administration of an effective amount of a tricyclic compound to the eye of an animal. This invention is more particularly pointed out in the appended claims and is described in its preferred embodiments in the following description.

BRIEF DESCRIPTION OF THE FIGURE

FIG. 1 shows the effect of tricyclic compounds amitriptyline, imipramine and nortriptyline in blocking axial growth.

DETAILED DESCRIPTION OF THE INVENTION

In the ordinary visual function of the eye of an animal, light forming an image passes through the lens and is received by the retina, a neural tissue embryologically related to the brain. The retina transmits this information to the optic nerve which sends it on to the brain.

Retinal neurochemicals (i.e., neuro-active chemical compounds) are key ingredients in the vision process. Specifically, light forming the image is sensed by the light receptors, the rods and cones, of the retina. These photoreceptors act as transducers changing light energy into electrical and/or chemical signals.

In the regular process of transmitting the image information to the brain, retinal nerve cells, in association with the photoreceptors, release neurochemicals and pass electrical signals transmitting information to adjacent retinal cells as parts of a network in the retina leading to the formulation and qualities of the signals that later go to the brain via optic nerve.

The present invention is directed to a method of controlling the abnormal postnatal growth of the eye of a maturing animal which comprises the ocular administration of therapeutically effective amounts of a tricyclic compound, of the class or classes usually termed tricyclic antidepressants, see for example Hoffmeister, F. and Stille, G. *Psychotropic*

*Agents, Part* 1: *Antipsychotics and Antidepressants,* Zeelen, F. J., Chapter 16, "Chemistry Structure and Activity" Springer-Verlag, New York, 1980. A method of inhibiting the abnormal postnatal axial growth of the eye of a maturing animal during conditions ordinarily leading to said abnormal growth, which comprises administering to said eye during postnatal maturation a therapeutically effective amount of a tricyclic compound in a carrier or diluent buffered to a pH suitable for ocular administration is also included in the present invention.

A composition for the inhibition of the abnormal postnatal axial growth of the eye of a maturing animal which comprises a pharmaceutically effective amount of a tricyclic compound present in a carrier or diluent buffered to a pH suitable for ocular administration is an embodiment of the present invention.

The present invention is also directed to a method of alleviating and controlling the development of amblyopia in the eye of a primate animal which comprises administering to such animal a therapeutically effective amount of a tricyclic compound.

Tricyclic compounds useful in the present invention include those compounds frequently used in psychiatry and generally termed tricyclic antidepressants. Tricyclic antidepressants, including and not limited to tertiary amines, secondary amines, and other active metabolites of these tricyclics are useful in the methods of the present invention. Particularly, tertiary amines, including and not limited to imipramine and amitriptyline; and secondary amines, including and not limited to nortriptyline and desipramine, and other active metabolites including and not limited to 10-hydroxynortriptyline have been found to be representative of the tricyclic compounds for use in the present invention.

Perhaps the best known tricyclics are the tertiary amines used in neuropsychiatry. The neuropharmacology of the tricyclic tertiary amines has been subject to intensive study in regard to their primary targets and their side effects. Amitriptyline and imipramine are representative examples of the class of tricyclics known as tertiary amines. These well known tricyclic antidepressants have complex metabolism in humans.

Two of the major pathways for the metabolism of tricyclic antidepressants are through 1) the mixed-function oxidase enzyme system, which hydroxylates aromatic rings, and 2) N-demethylation of one or both of the methyl groups associated with the side-chain amine. In both cases the products are often active pharmacologically.

Amitriptyline may be demethylated to the secondary amine, nortriptyline, an active metabolite, which in turn is converted to other active metabolites, including 10-hydroxynortriptyline. Desipramine, a secondary amine, is an active metabolite of the demethylation of imipramine. Not only are many tricyclic metabolites active against primary targets but they individually add to the recognized side effects of the family of compounds, notably as antagonists to neurohormonal receptors or as blockers of neurotransmitter reuptake systems. As receptor antagonists they vary in potency, affecting chiefly α-adrenergic, muscarinic and histaminergic receptors. So far as muscarinic subtypes are concerned, they are characterized as non-selective antagonists by McKinney et al. or as predominantly $M_2$ antagonists by Nomura et al. In varying degree they have been shown to block the central reuptake mechanism for 5-OH tryptamine (serotonin) dopamine and noradrenaline.

This invention is now described by the following example. This example is not to be construed as limiting the scope of the appended claims.

EXAMPLE

Form-deprivation myopia was induced in day-old White Leghorn chicks under aseptic conditions and ether anesthesia. One eyelid of the chicks was sutured which does not completely block vision. Translucent vision is permitted through the eyelid. The chicks were maintained on a 12 hour light:dark cycle. The sutured eyes were treated with either imipramine (2.5 µg), amitriptyline (2.48 µg), nortriptyline (2.37 µg), or saline solution. The contralateral unsutured open eye served as a control. The sample populations for imipramine, amitriptyline, and nortriptyline were n=8, n=6, and n=7 respectively. All agents were injected daily subconjunctivally during the light cycle. At two weeks of age the animals were sacrificed and axial and equatorial dimensions of unfixed eyes were measured with vernier calipers independently by two observers. Lid-sutured chick eyes treated with saline solution developed axial elongation while those treated with imipramine and amitriptyline had a virtual blockade of axial elongation. TABLE I illustrates the effects of drug therapy on the growth of lid-sutured chick eyes. The average increase in axial length is the difference, deprived eye minus contralateral unsutured eye, for the number (n) of animals tested.

TABLE I

| Drug | Dose (µg) | Increased Axial length | n | R |
|---|---|---|---|---|
| imipramine | 2.5 | 0.08 mm | 8 | p=<0.02 |
| amitriptyline | 2.48 | 0.00 mm | 9 | p=<0.002 |
| nortriptyline | 2.37 | 0.16 mm | 7 | |
| saline solution | — | 0.36 mm | 32 | |

Based on a one-way analysis of variance, there is significant effect on axial length ($p<0.02$ for imipramine at 2.5 µg/day and $p<0.002$ for amitriptyline at 2.48 µg/day). nortriptyline had a partial effect which, while not reaching statistical significance, exhibited a trend.

Treatment to inhibit axial elongation myopia during maturation of an animal can be administered by the use of the agent in eye drops. Indeed, in the vast majority of cases, treatment agents are administered to human eyes by the topical application of eye drops. Eye drops are typically made up at a concentration of active agent between about 0.1 and 2 percent in the ophthalmic medium. A 1 percent solution of imipramine, amitriptyline or other tricyclic compound in water would be a likely concentration for clinical use. Some constraints in ophthalmic formulation exist having to do with pH and preservative. A pH of about 6.5 is expected to be acceptable as an ophthalmic drop and practical in terms of known solubility and stability of imipramine. Phosphate buffering is also common for eye drops and may be necessary with tricyclic compounds. Other additives and ingredients may be present, e.g., such as those disclosed in Chiou, U.S. Pat. No. 4,865,599, at column 3, lines 7 to 50, which disclosure is incorporated herein by reference. A common regimen for application of eye drops is one to four times a day spaced evenly throughout waking hours. More effective agents may require fewer applications or enable the use of more dilute solutions. Alternatively, ointments, gels, solid inserts and local depositors of powders are now coming into increased use in clinical practice. Some avoid problems of drug decomposition while delivering a defined amount of drug. It is, of course, also possible to administer the above-described active agents in therapeutically effective amounts and dosages in pills, capsules, or other preparations for systemic administration. Administration may continue until such time as abnormal postnatal axial growth is corrected.

It should be noted that imipramine and amitriptyline share a good safety profile with other tricyclic antidepressant tertiary amines and secondary amines. They have been reported to be tolerated well in systemic use by most patients with minimal side effects.

In experiments in animals such as those mentioned hereinabove in which axial myopia has been experimentally induced by depriving the retina of formed images, it has been noted by others in primates that amblyopia was also experimentally and coincidentally induced. Amblyopia is evidenced by poor visual acuity in the eye resulting in poor visual performance. Normally, visual acuity improves during maturation. It is known that amblyopia may occur in humans from unknown causes or as part of strabismus. It is possible that administration of therapeutically effective amounts and dosages of the tertiary amine tricyclics, e.g., imipramine and amitriptyline, as well as their active metabolites, analogs and congeners, might prevent or inhibit the development of permanent or persistent amblyopia in maturing humans. It is also possible that humans who have already developed amblyopia from other or even unknown causes might be aided by similar therapeutic treatment with the aforementioned agents.

Various modifications of the invention in addition to those shown and described herein will be apparent to those skilled in the art from the foregoing description. Such modifications are also intended to fall within the scope of the appended claims.

What is claimed:

1. A method of controlling the abnormal postnatal growth of the eye of a maturing animal which comprises the ocular administration of therapeutically effective amounts of a muscarinic $M_2$ antagonist selected from the group consisting of imipramine, amitriptyline, nortriptyline, desipramine, and 10-hydroxynortriptyline in a carrier or diluent buffered to a pH suitable for ocular administration.

2. A method of inhibiting the abnormal postnatal growth of the eye of a maturing animal during conditions ordinarily leading to said abnormal growth, which comprises administering to said eye during postnatal maturation, a therapeutically effective amount of a muscarinic $M_2$ antagonist selected from the group consisting of imipramine, amitriptyline, nortriptyline, desipramine, and 10-hydroxynortriptyline, in a carrier or diluent buffered to a pH suitable for ocular administration.

3. The method of claim 2 wherein said muscarinic $M_2$ antagonist is imipramine.

4. The method of claim 2 wherein said muscarinic $M_2$ antagonist is amitriptyline.

5. The method of claim 2 wherein said muscarinic $M_2$ antagonist is nortriptyline.

6. The method of claim 2 wherein said muscarinic $M_2$ antagonist is desipramine.

7. The method of claim 2 wherein said muscarinic $M_2$ antagonist is 10-hydroxynortriptyline.

* * * * *